United States Patent [19]
Bothe

[11] Patent Number: 5,759,574
[45] Date of Patent: Jun. 2, 1998

[54] TEL-TALE-TABLETS

[76] Inventor: Steven T. Bothe, N27 W5230 Hamilton Rd., Cedarburg, Wis. 53012

[21] Appl. No.: 441,537

[22] Filed: May 15, 1995

[51] Int. Cl.[6] ............................. A61K 9/20; A61K 9/24
[52] U.S. Cl. ................................. 424/464; 424/472
[58] Field of Search ........................ 424/464, 465, 424/408, 472; 4/222

[56] References Cited

U.S. PATENT DOCUMENTS

| | | |
|---|---|---|
| 2,711,346 | 4/1955 | Irwin et al. |
| 3,048,526 | 8/1962 | Boswell. |
| 4,852,201 | 8/1989 | Wundrock et al. ............ 15/145 |
| 5,032,406 | 7/1991 | Dansereau et al. |
| 5,137,731 | 8/1992 | Casberg. |

*Primary Examiner*—Thurman K. Page
*Assistant Examiner*—Sharon Howard

[57] ABSTRACT

A toilet bowl sanitizing tablet that is constructed of solid, clear or white cleansing and/or deodorizing chemicals and has a smaller color core embedded in its center. This device when placed inside the toilet tank will slowly dissolve into the tank water, thus sanitizing the toilet bowl with clear, clean water with every flush. After weeks or months of use when the outer tablet has dissolved down to the center color core it will release its coloring agent to the water, thereby notifying the user the tablet has reached its depletion; eliminating the need to mark calendars, count flushes or periodically check inside the tank.

1 Claim, 1 Drawing Sheet

TEL-TALE-TABLETS

BACKGROUND AND SUMMARY OF THE INVENTION

Sanitizing and deodorizing devices for toilet bowls are widely used and come in a variety of types. Some of these devices consist of a block of chemical that slowly dissolves in the toilet tank. This type of device is generally clear or blue in color. The problem with the clear type is the failure of the product to notify the homeowner when it has completely devolved and is no longer sanitizing the bowl. The problem with the colored type is the staining of the toilet bowl by the coloring agent, the undesirable (to some) colored water in the toilet bowl, and, still no advanced warning of depletion. The only way to know when either of these types is nearing its end is to look inside the tank—an inconvenience.

Other types of devices are the mechanical type which dispense deodorizing and sanitizing solutions. These types of devices tend to be complicated and expensive.

Keeping the above in mind, it is the objective of this invention to provide an uncomplicated and economical method of sanitizing and deodorizing the toilet bowl and to provide a simple method of alerting the homeowner when replacement time is near.

To achieve the above, this invention consists of a small "color-core" centered in the block of clear sanitizing chemical. The block is placed in the toilet tank where it slowly devolves, releasing the cleaning chemicals. As the block nears depletion, the center "color-core" releases its color into the water, thereby alerting the homeowner that replacement time is near.

The center "color-core" is what makes this invention unique, allowing the homeowner to simply place the "Tel-Tale-Tablet" in the toilet tank and forget about it, eliminating the need to mark the calendar, count flushes, put up with color-stained toilet bowls or periodically check inside the toilet tank—the invention will alert you when its lifespan is nearing an end.

BRIEF DESCRIPTION OF THE DRAWINGS (FIG. 1 is a top view of the invention.)
(FIG. 2 is a side view of the invention)
Note: Both views show the location of the center Color Core.

DESCRIPTION OF THE PREFERRED EMBODIMENT

Figure 1:
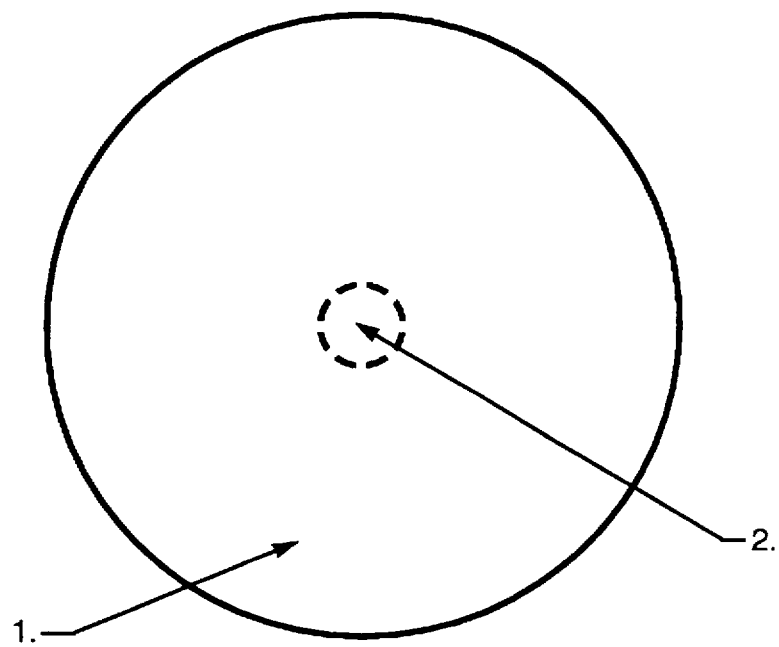
Figure 2:
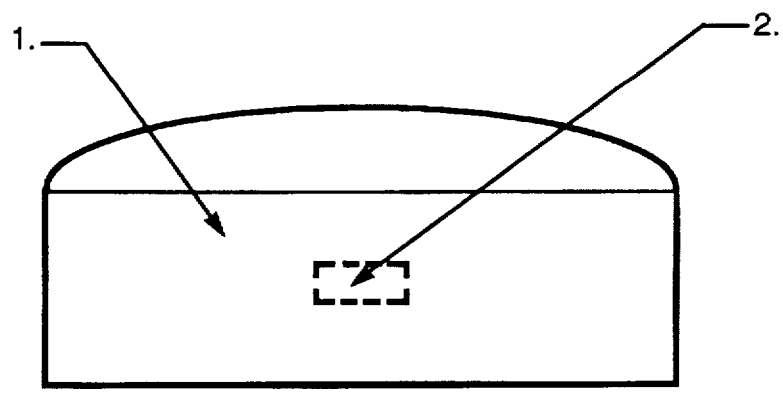

Turning next to the drawings in detail, FIG. 1 shows the Tel-Tale Tablet with its center color core. The tablet consists of a clear or white sanitizing and/or deodorizing chemical which slowly dissolves when placed inside the toilet water tank. This enhanced tank water then cleans and deodorizes the toilet bowl with each flush. The color core shown in FIG. 1 & 2 is located in the center of the tablet material and can consist of the same chemical make-up as the tablet with the addition of a coloring agent. Any color (other than white or clear) may be used for this center core.

FIG. 2 shows the side view of the invention with domed top. This domed design provides for a more even dissolving of the outer tablet. Other shapes and sizes are possible, each resulting in slightly different characteristics; this design (with its flat bottom and domed top) seems to work out the most efficiently. An even dissolving of the outer tablet is desired so the toilet tank water will not reach the center color core before the majority of the outer tablet has been used up.

Once the tablet has dissolved to this point, the tank water will reach the center color core shown in FIG. 1 & 2 and cause it to start dissolving, continuing to cleanse the water and also releasing its color to the water. This colored water will be released into the toilet bowl with each flush, notifying the homeowner the tablet is reaching its depletion. The color core can be made in various shapes and sizes depending on the duration of the warning desired.

As a result from the facts presented above, the invention being a toilet sanitizing device is more user-friendly than prior devices in that it allows the user to enjoy crystal-clear, sanitized toilet bowl water without the inconvenience of having to continually check inside the toilet tank or count flushes to know when the cleansing chemicals were depleted.

It is to be understood that the shape of the invention described above is given as a favorable example of the like, in that several alterations in the size and shape may be employed without deviating from the heart of the invention or focus of the subjoined claims.

I claim:

1. A toilet bowl water sanitizing device for use in the toilet tank consisting of a tablet with a dome top made of solid cleansing chemicals, clear or white in color and having a smaller different color core embedded in its center said device will sanitize and/or deodorize the toilet bowl by dissolving slowly in the tank over a period of weeks or months, releasing its cleansing agents to the toilet bowl.

* * * * *